US008563581B2

(12) United States Patent
Habash et al.

(10) Patent No.: US 8,563,581 B2
(45) Date of Patent: Oct. 22, 2013

(54) NITROXIDES FOR USE IN TREATING PREDISPOSED OR AT RISK PATIENTS

(75) Inventors: Louis Habash, Newport Coast, CA (US); Clarence Jones, Huntington Beach, CA (US)

(73) Assignee: Mitos Pharmaceuticals, Inc., Newport Beach, CA (US)

( * ) Notice: Subject to any disclaimer, the term of this patent is extended or adjusted under 35 U.S.C. 154(b) by 986 days.

(21) Appl. No.: 11/815,440

(22) PCT Filed: Feb. 2, 2006

(86) PCT No.: PCT/US2006/003696
§ 371 (c)(1),
(2), (4) Date: Mar. 4, 2008

(87) PCT Pub. No.: WO2006/084041
PCT Pub. Date: Aug. 10, 2006

(65) Prior Publication Data
US 2008/0319014 A1 Dec. 25, 2008

Related U.S. Application Data

(60) Provisional application No. 60/649,194, filed on Feb. 2, 2005.

(51) Int. Cl.
*A61K 31/445* (2006.01)
*A61P 3/10* (2006.01)

(52) U.S. Cl.
USPC ......................................................... 514/315

(58) Field of Classification Search
USPC ......................................................... 514/315
See application file for complete search history.

(56) References Cited

U.S. PATENT DOCUMENTS

| 5,622,994 | A | | 4/1997 | Carney et al. | |
| 5,858,977 | A | * | 1/1999 | Aukerman et al. | ............. 514/12 |
| 6,096,759 | A | | 8/2000 | Wilcox | |
| 6,617,337 | B1 | | 9/2003 | Wilcox | |
| 2002/0091266 | A1 | | 7/2002 | Anggard et al. | |
| 2005/0048565 | A1 | * | 3/2005 | Tomita et al. | ................. 435/7.1 |

FOREIGN PATENT DOCUMENTS

WO   WO 02/26231   *   4/2002

OTHER PUBLICATIONS

S Werner, Induction of keratinocyte growth factor expression is reduced and delayed during wound healing in the genetically diabetic mouse. J Invest Dermatol 103: 469-473 (1994).*
AW Hart, Attenuation of FGF signalling in mouse beta-cells leads to diabetes. Nature 408: 864-868 (2000).*
J Movassat, Keratinocyte growth factor and beta cell differentiation in human fetal pancreatic endocrine precursor cells. Diabetologia 46: 822-829 (2003).*
Database BIOSIS, Accession No. 2004:283559, Jagadeesha, et al., "Scavenging superoxide with Tempol inhibits vascular smooth muscle cell apoptosis and neointima formation following vascular injury in type 2 diabetic rats"; FASEB Journal, (2004) vol. 18, No. 4-5, pp. 709.
Database BIOSIS, Accession No. 2004:289112, Bast, et al., "Impaired renal preglomerular response to depolarization in diabetes: potential roles of extracellular glucose and oxidative stress"; FASEB Journal, (2004) vol. 18, No. 4-5, pp. 205.

* cited by examiner

*Primary Examiner* — Jeffrey S. Lundgren
*Assistant Examiner* — Sara E Townsley
(74) *Attorney, Agent, or Firm* — Knobbe Martens Olson & Bear LLP

(57) ABSTRACT

Pharmaceutical compositions are provided that are useful in treating diabetes. The compositions comprise a pharmaceutically acceptable carrier, and an effective therapeutic or prophylactic amount of a nitroxide antioxidant that alters the expression of genes related to diabetes. Methods are also provided for the use of the pharmaceutical compositions in the treatment or prevention of diabetes. In a preferred embodiment, the nitroxide antioxidant is Tempol (4-hydroxy-2,2,6,6-tetramethylpiperidine-1-oxyl).

21 Claims, No Drawings

NITROXIDES FOR USE IN TREATING PREDISPOSED OR AT RISK PATIENTS

BACKGROUND OF THE INVENTION

1. Field of the Invention

The present invention relates to pharmaceutical compositions useful for treating or preventing diabetes, and to methods for using these compositions in treating or preventing diabetes.

2. Description of the Related Art

Diabetes mellitus is an umbrella term for a number of metabolic disorders, all of which share the common symptom of hyperglycemia. It is classified into two broad categories: type I, which generally results from autoimmune destruction of the pancreatic beta cells that produce insulin and is characterized by insulin deficiency and a tendency to develop ketosis, and type II, which results from a variety of genetic and metabolic defects in insulin action and/or secretion and is characterized by variable degrees of insulin resistance, impaired insulin secretion, and increased glucose production.

Diabetes is prevalent worldwide and the incidence of the disease has risen dramatically over the past two decades. In the United States, approximately 6% of the population has diabetes, and approximately 800,000 new cases occur each year. The prevalence of the disease is approximately two times higher among African Americans, Native Americans, and Hispanic Americans that among non-Hispanic whites.

Individuals with diabetes are often unaware that they have the disorder; studies have suggested that type 2 diabetes may be present for up to a decade before diagnosis, and as many as half of type 2 diabetes patients have one or more diabetes-related complications (e.g., eye disease, sensory and motor neuropathy, nephropathy, vascular disease, gastrointestinal or genitourinary dysfunction). Screening using a fasting plasma glucose test is commonly employed to diagnose such "silent" cases of the disease.

Long-term management of diabetes is complex and the active participation of the patient is crucial for success. It involves individualized nutritional and exercise regiments, with patient self-monitoring of glucose levels and, where appropriate, self-administration of insulin preparations. Failure to comply with the therapeutic program is a frequent problem, and depression and eating disorders are often encountered.

Diabetes is, thus, a very common disease presenting serious potential complications, which is difficult to manage. It would be desirable to avoid these issues by developing methods of directly curing the insulin-related problems that give rise to them. One potential way to do so is to use genetic therapy to target the cellular dysfunction that causes diabetes. To this end, it would be desirable to identify genes related to diabetes and develop methods of altering the expression patterns of those genes so as to prevent the development of the disease or reduce its effects once it has occurred.

SUMMARY OF THE INVENTION

Pharmaceutical compositions are provided that are useful in preventing and treating diabetes. The compositions comprise a pharmaceutically acceptable carrier, and an effective therapeutic or prophylactic amount of an agent that changes the expression pattern of a gene related to diabetes. Methods are also provided for the use of the pharmaceutical compositions in the alteration of intracellular levels of diabetes-related proteins. In a preferred embodiment, the agent is a nitroxide antioxidant, such as Tempol (4-hydroxy-2,2,6,6-tetramethylpiperidine-1-oxyl).

DETAILED DESCRIPTION OF THE PREFERRED EMBODIMENT

As described above, a composition and method are disclosed which are useful in treating or preventing diabetes. In a preferred embodiment, the agent used to change the expression pattern of a gene related to diabetes is a nitroxide antioxidant. Tempol is a stable nitroxide radical characterized by the chemical formula 4-hydroxy-2,2,6,6-tetramethylpiperidine-1-oxyl that has antioxidative properties. The present applicants have discovered that Tempol also possesses the novel property of altering the expression of genes encoding for proteins associated with the amelioration of diabetes (see Tables 1 and 2 below). Previous therapies have generally not focused on altering the expression patterns of such diabetes-related genes.

The use of other nitroxide compounds is also contemplated. According to certain embodiments the nitroxide compound can be selected from the following formulas:

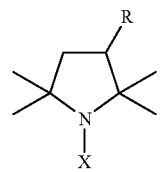

Wherein X is selected from O. and OH, and R is selected from COOH, CONH, CN, and $CH_2NH_2$.

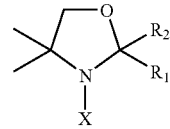

Wherein X is selected from O. and OH, and $R_1$ is selected from $CH_3$ and spirocyclohexyl, and $R_2$ is selected from $C_2H_5$ and spirocyclohexyl.

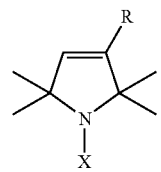

Wherein X is selected from O. and OH and R is selected from CONH.

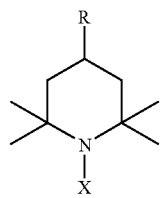

Wherein X is selected from O. and OH and R is selected from H, OH, and $NH_2$.

Suitable nitroxide compounds can also be found in Proctor, U.S. Pat. No. 5,352,442, and Mitchell et al., U.S. Pat. No. 5,462,946, both of which are hereby incorporated by reference in their entireties.

A non-limiting list of nitroxide compounds include: 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4amino-2,2,6,6-tetramethyl-1-piperidinyloxy (Tempamine), 3-Aminomethyl-PROXYL, 3-Cyano -PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, and the like.

Experimental Protocol

To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that a gene related to diabetes, keratinocyte growth factor (KGF; also known as fibroblast growth factor-7), exhibited a more than twofold increase in expression. This gene is shown in Table 1.

In a further gene expression study, Tempol was administered to experimental mice at a dose of 5 g/kg of diet from 12 months through 15 months. Mice receiving the same diet without the addition of Tempol were used as a negative control. At the age of 15 months, the adipose tissue of the experimental animals was obtained. The expression of a broad spectrum of genes in the adipose tissue was assessed using chip-based microarray technology. Specifically, in this case an Affymetrix MOE430A 2.0 array, containing 12,960 genes, was employed. Such chips are well known in the art and are widely used to assess gene expression. The experimental results on the adipose tissue show that a gene related to diabetes, adiponectin (C1Q and collagen domain containing) (ADIPOQ) exhibited an increase in expression. This gene is shown in Table 2.

TABLE 1

DIABETES-RELATED GENE EXIBITING INCREASED EXPRESSION IN CARDIAC TISSUE AFTER TEMPOL ADMINISTRATION

| ORF | Description | Control mice | | | TEMPOL-treated mice | | | Fold change |
|---|---|---|---|---|---|---|---|---|
| | | tpc1 | tpc2 | tpc3 | tp51 | tp52 | tp53 | |
| Z22703 | Keratinocyte Growth Factor (Fibroblast Growth Factor 7) | 49 | 21 | 45 | 13 | 52 | 96 | 2.1 |

TABLE 2

DIABETES-RELATED GENE EXHIBITING INCREASED EXPRESSION IN ADIPOSE TISSUE AFTER TEMPOL ADMINISTRATION

| Description | Mean (Tempol-treated mice) | Mean (Control mice) | P Value | Fold change |
|---|---|---|---|---|
| Adiponectin, C1Q and collagen domain containing | 33876 | 27698 | 0.003 | 1.22 |

A short summary of the genes described in Tables 1 and 2 is provided below.

Keratinocyte Growth Factor (Fibroblast Growth Factor 7)

KGF is a member of the heparin-binding fibroblast growth factor family and was originally isolated from a human lung fibroblast cell line. It exhibits a high degree of specificity for epithelial cells both in vitro and in vivo. A recent study investigated the effects of KGF on beta-cell growth and differentiation on islet-like cell clusters derived from human fetal pancreas. (Movassat et al., Diabetologia 46:822-829 (2003)) Although the exposure of human fetal beta-islet cells to KGF under culture conditions had no effect on the number of insulin producing cells as measured by insulin or DNA content, increased numbers of beta cells were found in 8-week xenografts from Rowlett athymic nude rats given KGF for 10 consecutive days beginning 48 hours after human fetal islet cell transplantation. This was found to be the result of KGF-induced proliferation of pancreatic ductal cells and the differentiation thereof into functional beta cells. Moreover, when KGF-treated animals were challenged with glucose, it was shown that the transplanted cells were fully capable of producing insulin, unlike the control group, in which the grafts were incompetent in this regard. Increasing the concentration of KGF, for example by the administration of Tempol, thus offers the possibility of counteracting the pathology giving rise to diabetes.

As shown in Table 1, the expression of HGF in the cardiac tissue of the experimental mice was increased 2.1-fold in the animals treated with Tempol.

Adiponectin, C1Q and Collagen Domain Containing

Adiponectin is an adipokine that is secreted specifically from differentiated adipocytes. Adiponectin is found in serum at concentrations up to 10 µg/ml. Adiponectin is present at reduced levels in the plasma of patients with diabetes. Furthermore, administration of exogenous adiponectin has been shown to correct metabolic defects that are associated with insulin resistance. (Hug et al., Current Opinion in Pharmacology 5 (2005) 129-134) A decrease in adiponectin level has been implicated in the development of insulin resistance. (Hotta et al., Diabetes 50 (2001) 1126-1133) It has been suggested that adiponectin and TNF-α act in counter regulatory pathways and that the net balance of their actions results in the proper homeostasis of glucose and fatty acid metabolisms. When adiponectin levels decline in the serum, as for example in obesity, the adipose TNF-α activity could lead to a shift toward insulin resistance. (Hug et al., Current Opinion In Pharmacology 5 (2005) at 131-132) Increasing the serum concentration of adiponectin, for example by the administration of Tempol, thus offers the possibility of reestablishing the balance in the regulatory pathways and halting the shift toward insulin resistance.

As shown in Table 2, the expression of adiponectin in the adipose tissue of the experimental mice was increased 1.22-fold in the animals treated with Tempol.

Preferred Embodiment: Diabetes Prophylaxis and Treatment Protocol

As described above, Tempol has the effect of increasing the expression level of KGF and adiponectin, genes related to diabetes. Since the expression of these genes is increased, administration of Tempol will have a beneficial effect by increasing concentrations of gene products that are beneficial in counteracting the disease. In a preferred embodiment of the present invention, therefore, Tempol is administered to a mammalian host, such as a human, exhibiting no symptoms of diabetes in order to prevent the development of diabetes. Particularly preferred patients are those who are predisposed or otherwise at risk for diabetes, such as those with a family history of diabetes or those with genetic or serum markers associated with diabetes. Alternatively, Tempol may be administered to a human exhibiting diabetes in order to ameliorate the effects of the disease on the patient. For this purpose, Tempol, non-toxic salts thereof, acid addition salts thereof or hydrates thereof may be administered systemically or locally, usually by oral or parenteral administration.

The doses to be administered are determined depending upon, for example, age, body weight, symptom, the desired therapeutic effect, the route of administration, and the duration of the treatment. In the human adult, the dose per person at a time is generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time is generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration is also contemplated for from 1 to 24 hours per day to achieve a target concentration from about 0.01 mg/L to about 100 mg/L. Specific examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does, however, depend upon various conditions, and there may be cases wherein doses lower than or greater than the ranges specified above are used.

Tempol may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, Tempol is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. In injections, Tempol may be dissolved, suspended and emulsified in a solvent. The solvents are, for example, distilled water for injection, physiological salt solution, vegetable oil, propylene glycol, polyethylene glycol, alcohol such as ethanol, or a mixture thereof. Moreover the injections may also include stabilizing agents, agents to assist dissolution (e.g. glutamic acid, aspartic acid or POLYSORBATE80 (registered trade mark)), suspending agents, emulsifying agents, soothing agents, buffer agents, preserving agents, etc. They are sterilized in the final process or manufactured and prepared by sterile procedure. They may also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise Tempol and are administered by methods known in the art.

Spray compositions may comprise additional substances other than diluents: e.g. stabilizing agents (e.g. sodium sulfite hydride), isotonic buffers (e.g. sodium chloride, sodium citrate or citric acid). For preparation of such spray compositions, for example, the method described in U.S. Pat. Nos. 2,868,691 or 3,095,355 may be used. Briefly, a small aerosol particle size useful for effective distribution of the medicament may be obtained by employing self-propelling compositions containing the drugs in micronized form dispersed in a propellant composition. Effective dispersion of the finely divided drug particles may be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size is less than about 5 microns. The propellant composition may employ, as the suspending agent, a fatty alcohol such as oleyl alcohol. The minimum quantity of suspending agent is approximately 0.1 to 0.2 percent by weight of the total composition. The amount of suspending agent is preferably less than about 4 percent by weight of the total composition to maintain an upper particle size limit of less than 10 microns, and preferably 5 microns. Propellants that may be employed include hydrofluoroalkane propellants and chlorofluorocarbon propellants. Dry powder inhalation may also be employed.

EXAMPLE 1

A 70-kilogram diabetic patient is administered a dose of 1500 mg of Tempol per day for 180 days. This may be administered in a single dose, or may be administered as a number of smaller doses over a 24-hour period: for example, three 500-mg doses at eight-hour intervals. Following treatment, the protein level of keratinocyte growth factor in the pancreatic ductal cells, and the serum level of adiponectin, is increased.

EXAMPLE 2

A 70-kilogram patient at risk for but not yet diagnosed with diabetes is administered a dose of 1500 mg of Tempol per day for 180 days. This may be administered in a single dose, or may be administered as a number of smaller doses over a 24-hour period: for example, three 500-mg doses at eight-hour intervals. Following treatment, the protein level of keratinocyte growth factor in the pancreatic ductal cells, and the serum level of adiponectin, is increased.

What is claimed is:

1. A method of treatment comprising:

identifying a subject predisposed to or at risk for developing diabetes wherein the subject exhibits no symptoms of diabetes; and administering to the subject an amount of 4-hydroxy-2,2,6,6-tetramethylpiperidine-1-oxyl effective to increase proliferation of pancreatic beta cells, ameliorate insulin resistance, increase intracellular levels of adiponectin or keratinocyte growth factor, or increase expression of an adiponectin or keratinocyte growth factor gene in the subject.

2. The method of claim 1, wherein the intracellular levels of keratinocyte growth factor are increased.

3. The method of claim 1, wherein the intracellular levels of adiponectin are increased.

4. The method of claim 1, wherein the effective amount of 4-hydroxy-2,2,6,6-tetramethylpiperidine-1-oxyl is within the range of 0.01-300 mg/kg.

5. The method of claim 1, wherein the effective amount of 4-hydroxy-2,2,6,6-tetramethylpiperidine-1-oxyl is within the range of 0.1-250 mg/kg.

6. The method of claim 1, wherein the effective amount of 4-hydroxy-2,2,6,6-tetramethylpiperidine-1-oxyl is within the range of 1-200 mg/kg.

7. The method of claim 1, wherein the effective amount of 4-hydroxy-2,2,6,6-tetramethylpiperidine-1-oxyl is within the range of 2-150 mg/kg.

8. The method of claim 1, wherein the effective amount of 4-hydroxy-2,2,6,6-tetramethylpiperidine-1-oxyl is within the range of 5-125 mg/kg.

9. The method of claim 1, wherein the effective amount of 4-hydroxy-2,2,6,6-tetramethylpiperidine-1-oxyl is within the range of 7-100 mg/kg.

10. The method of claim 1, wherein the effective amount of 4-hydroxy-2,2,6,6-tetramethylpiperidine-1-oxyl is within the range of 10-75 mg/kg.

11. The method of claim 1, wherein the effective amount of 4-hydroxy-2,2,6,6-tetramethylpiperidine-1-oxyl is within the range of 15-30 mg/kg.

12. The method of claim 1, wherein expression of the keratinocyte growth factor gene is increased.

13. The method of claim 1, wherein expression of the adiponectin gene is increased.

14. The method of claim 1, wherein the proliferation of pancreatic beta cells is increased.

15. The method of claim 1, wherein insulin resistance is ameliorated.

16. The method of claim 1 wherein the subject predisposed to or at risk for developing diabetes has abnormally depressed levels of adiponectin due to abnormally high levels of adipose tissue; and wherein 4-hydroxy-2,2,6,6-tetramethylpiperidine-1-oxyl is an amount effective to increase intracellular levels of adiponectin or increase expression of an adiponectin gene in the subject.

17. The method of claim 1 wherein the subject is obese.

18. A method of treatment comprising:

identifying a subject with abnormally depressed levels of adiponectin due to abnormally high levels of adipose tissue, wherein the subject exhibits no symptoms of diabetes; and administering to the subject an amount of 4-hydroxy-2,2,6,6-tetramethylpiperidine-1-oxyl effective to increase intracellular levels of adiponectin or to increase expression of an adiponectin gene in the subject.

19. The method of claim 18 wherein the subject is obese.

20. A method of treatment comprising:

identifying a subject with abnormally high levels of adipose tissue, wherein the subject exhibits no symptoms of diabetes; and administering to the subject an amount of 4-hydroxy-2,2,6,6-tetramethylpiperidine-1-oxyl effective to increase intracellular levels of adiponectin or to increase expression of an adiponectin gene in the subject.

21. The method of claim 20 wherein the subject is obese.

* * * * *